(12) United States Patent
Yamazaki

(10) Patent No.: US 7,897,614 B2
(45) Date of Patent: Mar. 1, 2011

(54) PREVENTIVE AGENT/REMEDIAL AGENT FOR CONSTIPATION PREDOMINANT IBS

(75) Inventor: Satoshi Yamazaki, Tokyo (JP)

(73) Assignee: Mitsubishi Tanabe Pharma Corporation, Osaka (JP)

( * ) Notice: Subject to any disclaimer, the term of this patent is extended or adjusted under 35 U.S.C. 154(b) by 438 days.

(21) Appl. No.: 11/514,905

(22) Filed: Sep. 5, 2006

(65) Prior Publication Data

US 2007/0004770 A1   Jan. 4, 2007

Related U.S. Application Data

(63) Continuation of application No. 10/487,491, filed as application No. PCT/JP02/02402 on Mar. 14, 2002, now abandoned.

(30) Foreign Application Priority Data

Aug. 24, 2001   (JP) .............................. 2001-254662

(51) Int. Cl.
A61K 31/4365 (2006.01)
C07D 401/02 (2006.01)

(52) U.S. Cl. ...................... 514/301; 546/114

(58) Field of Classification Search ................. 514/301; 546/114

See application file for complete search history.

(56) References Cited

U.S. PATENT DOCUMENTS 5,352,685 A   10/1994   Maruyama et al.

FOREIGN PATENT DOCUMENTS

| EP | 0 560 348 | 9/1993 |
|---|---|---|
| JP | 08-286450 | 4/1996 |
| JP | 8/143573 | 6/1996 |
| WO | 01/37824 | 5/2001 |
| WO | 01/58898 | 8/2001 |

OTHER PUBLICATIONS

Irritable Bowel Syndrome (IBS) by International foundation for Functional Gastrointestinal Disorders, Nov. 2007.*
West, Anthony R., Solid State Chemistry and its Applications, Wiley, New York, 1988, pp. 358 & 365.*
About GI Motility, Jun. 26, 2008, International foundation of funtional Gastrointestinal Disorders by IFFGD.*
Revel et al., Drugs of the Future, "MKC-733: Treatment of GERD Treatment of Constipation 5-HT$_3$ Receptor Agonist" 1999, 24(9), pp. 966-968, and corresponding abstract.
U.S. Appl. No. 10/203,278, Jul. 10, 2003.
Bueno et al., "Gastrointestinal Pharmacology: Irritable Bowel Syndrome", Current Opinion in Pharmacology, 2005, 5:583-588.

* cited by examiner

*Primary Examiner*—Rita J Desai
(74) *Attorney, Agent, or Firm*—Wenderoth, Lind & Ponack, L.L.P.

(57) ABSTRACT

A novel preventive and/or therapeutic medicament for a constipation predominant IBS which contains as the active ingredient a thieno[3,2-b]pyridinecarboxamide derivative represented by the formula (I):

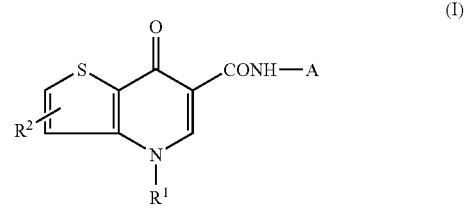

wherein $R^1$ and $R^2$ each independently represents hydrogen atom or a lower alkyl group and A represents a substituent selected from the group consisting of 1-azabicyclo[3.2.2] nonyl group 1-azabicyclo[2.2.2]octyl group, and the N-oxides thereof, a pharmaceutically acceptable salt thereof, or a solvate or hydrate thereof.

21 Claims, 1 Drawing Sheet

PREVENTIVE AGENT/REMEDIAL AGENT FOR CONSTIPATION PREDOMINANT IBS

This application is a continuation application of Ser. No. 10/487,491 filed Feb. 23, 2004, now abandoned which is a U.S. National Stage Application of International Application No. PCT/JP02/02402 filed Mar. 14, 2002.

TECHNICAL FIELD

This invention relates to a medicament which is useful for preventing and treating irritable bowel syndromes (hereinafter abbreviated to IBS). In more detail, this invention relates to a medicament comprising specific thieno[3,2-b]pyridinecarboxamide compound as an active ingredient which is useful for preventing and treating a constipation predominant IBS.

BACKGROUND ART

IBS is a syndrome defined as a functional disorder in which abdominal symptoms consisting mainly of abdominal pain and irregular bowel movement continue but organic disorders as causes therefor cannot be identified (Clinical Gastroenterology, 2000, VOL. 15, No. 13, p. 1607). It is often associated with psychological manifestations such as anxiety and depression.

According to Rome II which are diagnostic criteria for all the functional digestive disorders, when "no organic disorders are found in spite of the existence of lower gastrointestinal symptoms", such a condition is diagnosed as functional bowel disorders. The functional bowel disorders are divided further into IBS, functional diarrhea, functional constipation, and functional abdominal bloating based on their characteristic syndromes. In brief, the functional diarrhea is chronic diarrhea not accompanied with abdominal pain, the functional constipation is chronic constipation not accompanied with abdominal pain and the functional abdominal bloating is a group of disorders having not abdominal pain but abdominal distension and gas as cardinal symptoms (Clinical Gastroenterology, 2000, VOL. 15, No. 13, p. 1698). IBS is a disorder which is not included in any one of the functional diarrhea, functional constipation and functional abdominal bloating so that it can be considered as a generic name of diarrhea accompanied with abdominal pain (diarrhea predominant IBS), constipation accompanied with abdominal pain (constipation predominant IBS), and disorders (alternating IBS) which are accompanied with abdominal pain, and alternating diarrhea and constipation.

At present, there exists no eradicative drug for IBS and symptomatic treatment have been conducted for aiming at amelioration of symptoms of each disorder. Each type of IBS will next be described more specifically. In diarrhea predominant IBS, frequent diarrhea with small volumes of stool occurs continuously over a long period. For this diarrhea predominant IBS, an anticholinergic agent capable of controlling the contraction of smooth muscle and having antispastic action has been popularly employed. In many cases, antiflatulents are used in combination. Constipation predominant IBS is spastic constipation caused by acceleration of the bowel motility. For this constipation predominant IBS, a method of adjusting the hardness of stool by using a saline laxative is frequently employed. In alternating IBS, diarrhea and constipation occur alternately. It is therefore difficult to treat it with one drug and usually a prokinetic agent is employed.

Japanese Patent Unexamined Publication (Kokai) No. Hei 5-310747 discloses that the compounds of the present invention enhance the gastric motility, more specifically, the compounds of the present invention accelerate gastric emptying in male ddy mice, accelerate gastric contraction in the dog with a strain gauge force transducer attached thereto, and have 5-$HT_3$ (serotonin 3) receptor antagonistic activity in the Bezold-Jarisch reflex test. This publication however includes neither suggestion nor teaching on the relationship between the compounds of the present invention and bowel function.

Japanese Patent Unexamined Publication (Kokai) No. Hei 8-143573 discloses an invention concerning a preventive or therapeutic agent for diseases of intestinal motility dysfunction, which comprises, as an active ingredient, the above-described thieno[3,2-b]pyridinecarboxamide compound. Specific examples of the diseases of intestinal motility dysfunction include atonic constipation, spastic constipation and rectal constipation. Only Example 2 of Japanese Patent Unexamined Publication (Kokai) No. Hei 8-143573, however, directly shows that the compound is effective for constipation. A disease model used in this example should be an atonic constipation model, because clonidine for relaxing intestine was applied as the drug thereto. This publication only suggests that the compound of the present invention is effective for atonic constipation and does not include a specific disclosure about the effectiveness of the compound for constipation predominant IBS (as described above, constipation predominant IBS can be considered as spastic constipation)

On the contrary the present invention has firstly and experimentally revealed that the specific thieno[3,2-b]pyridinecarboxamide compounds are effective against the constipation predominant IBS by administering said compounds to human constipation predominant IBS patients.

The purpose of the present invention is to provide to a medicament for preventing and/or treating constipation predominant IBS containing the specific thieno[3,2-b]pyridinecarboxamide compounds as the active ingredients.

DISCLOSURE OF THE INVENTION

When the compound of the present invention was administered to human patients suffered from constipation predominant IBS, the compound of the present invention exhibited superior effects against the patients suffered from constipation predominant IBS and the present invention was achieved on the basis of these findings.

The gist of the present is as follows:

1. A preventive and/or therapeutic medicament for a constipation predominant IBS which comprises as an active ingredient a thieno[3,2-b]pyridinecarboxamide derivative represented by the following formula (I) or a pharmaceutically acceptable salt thereof, or any solvate or hydrate thereof:

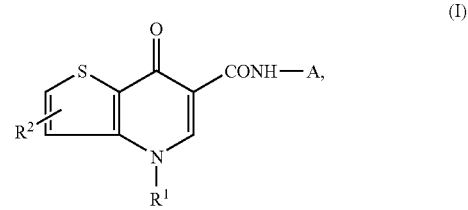

wherein $R^1$ and $R^2$ each independently represents hydrogen atom or a lower alkyl group and A represents a substituent selected from the group consisting of 1-azabicyclo[3.2.2] nonyl group, 1-azabicyclo[2.2.2]octyl group, and an N-oxides thereof.

2. The preventive and/or therapeutic medicament as mentioned above, wherein $R^1$ and $R^2$ each independently represents hydrogen atom or methyl group.

3. The preventive and/or therapeutic medicament as mentioned above, wherein A represents 1-azabicyclo[2.2.2]oct-3-yl group or N-oxide thereof.

4. The preventive and/or therapeutic medicament as mentioned above, wherein the compound of the aforementioned formula (I) is any one of N-(1-azabicyclo[2.2.2]oct-3-yl)-4,7-dihydro-7-oxo-thieno[3,2-b]pyridine-6-carboxamide, (R)-N-(1-azabicyclo[2.2.2]oct-3-yl)-4,7-dihydro-7-oxo-thieno[3,2-b]pyridine-6-carboxamide, (S)-N-(1-azabicyclo[2.2.2]oct-3-yl)-4,7-dihydro-7-oxo-thieno[3,2-b]-pyridine-6-carboxamide.

5. The preventive and/or therapeutic medicament as mentioned above, wherein the compound of the formula as mentioned above is in the form of hydrochloride.

6. The preventive and/or therapeutic medicament as mentioned above, wherein the compound of the aforementioned formula (I) is (R)-N-(1-azabicyclo[2.2.2]oct-3-yl)-4,7-dihydro-7-oxo-thieno[3,2-b]pyridine-6-carboxamide hydrochloride.

As the active ingredient of the preventive and/or therapeutic medicament of the present invention, one or not less than two compounds falling within the thieno[3,2-b]pyridinecarboxamide compounds represented by the above mentioned formula. In the formula, the lower alkyl group in $R^1$ and $R^2$ includes a $C_{1-6}$ alkyl group, preferably a $C_{1-4}$ alkyl group such as methyl group, ethyl group, n-propyl group, I-propyl group, n-butyl group, sec-butyl group, tert-butyl group or the like. Among them, methyl group is preferred. The compounds wherein both $R^1$ and $R^2$ are hydrogen atoms are also preferable active ingredients of the medicaments of the present invention. When $R^2$ represents a lower alkyl group, $R^2$ may substitute on either of the 2-position or 3-position of the thieno[3,2-b]pyridine ring.

In the aforementioned formula (I), A represents 1-azabicyclo[3.2.2]nonyl group or 1-azabicyclo[2.2.2]octyl group, preferably 1-azabicyclo[2.2.2]octyl group, or a substituent wherein the nitrogen atom of these groups forms an N-oxide. A bond of the substituent A and the carboxamide group of the compound of the formula (I) is formed by any carbon atom of the substituent A and the nitrogen atom of the carboxamide group. For example, the substituent A can include 1-azabicyclo[2.2.2]oct-2-yl group, 1-azabicyclo[2.2.2]oct-3-yl group, 1-azabicyclo[2.2.2]oct-4-yl group, 1-azabicyclo[3.2.2]non-2-yl group, 1-azabicyclo[3.2.2]non-3-yl group, 1-azabicyclo[3.2.2]non-4-yl group, 1-azabicyclo[3.2.2]non-5-yl group, 1-azabicyclo[3.2.2]non-6-yl group, 1-azabicyclo[3.2.2]non-7-yl group, and the groups of N-oxide thereof. The preferable example includes 1-azabicyclo[2.2.2]oct-3-yl group.

The configuration of a carbon atom of the substituent A that binds to the nitrogen atom of the carboxamide group is not particularly limited, and the atom may be in either R-configuration or S-configuration. The substituent A may be used a racemate or a mixture in any ratio of optical isomers. When an optically active substituent A is used, those wherein the absolute configuration of the above carbon atom is R-configuration are preferably used.

Among the compounds as the active ingredients of the preventive medicaments and/or the therapeutic medicaments of the present invention, the particularly preferable compounds include racemates, or any optically active isomers, or N-oxides thereof such as N-(1-azabicyclo[2,2,2]oct-3-yl)-4,7-dihydro-7-oxo-thieno[3,2-b]pyridine-6-carboxamide;
N-(1-azabicyclo[2,2,2]oct-3-yl)-4,7-dihydro-4-methyl-7-oxo-thieno[3,2-b]pyridine-6-carboxamide;
N-(1-azabicyclo[2,2,2]oct-3-yl)-4,7-dihydro-4-ethyl-7-oxo-thieno[3,2-b]pyridine-6-carboxamide;
N-(1-azabicyclo[2,2,2]oct-3-yl)-4,7-dihydro-2,4-dimethyl-7-oxo-thieno[3,2-b]pyridine-6-carboxamide;
N-(1-azabicyclo[2,2,2]oct-3-yl)-4,7-dihydro-3,4-dimethyl-7-oxo-thieno[3,2-b]pyridine-6-carboxamide;
N-(1-azabicyclo[2,2,2]oct-3-yl)-4,7-dihydro-4-ethyl-2-methyl-7-oxo-thieno[3,2-b]pyridine-6-carboxamide;
N-(1-azabicyclo[2,2,2]oct-2-yl)-4,7-dihydro-7-oxo-thieno[3,2-b]pyridine-6-carboxamide;
N-(1-azabicyclo[2,2,2]oct-2-yl)-4,7-dihydro-4-methyl-7-oxo-thieno[3,2-b]pyridine-6-carboxamide;
N-(1-azabicyclo[2,2,2]oct-2-yl)-4,7-dihydro-4-ethyl-7-oxo-thieno[3,2-b]pyridine-6-carboxamide;
N-(1-azabicyclo[2,2,2]oct-2-yl)-4,7-dihydro-2,4-dimethyl-7-oxo-thieno[3,2-b]pyridine-6-carboxamide;
N-(1-azabicyclo[2,2,2]oct-2-yl)-4,7-dihydro-3,4-dimethyl-7-oxo-thieno[3,2-b]pyridine-6-carboxamide;
N-(1-azabicyclo[2,2,2]oct-2-yl)-4,7-dihydro-4-ethyl-2-methyl-7-oxo-thieno[3,2-b]pyridine-6-carboxamide;
N-(1-azabicyclo[2,2,2]oct-4-yl)-4,7-dihydro-7-oxo-thieno[3,2-b]pyridine-6-carboxamide;
N-(1-azabicyclo[2,2,2]oct-4-yl)-4,7-dihydro-4-methyl-7-oxo-thieno[3,2-b]pyridine-6-carboxamide;
N-(1-azabicyclo[2,2,2]oct-4-yl)-4,7-dihydro-4-ethyl-7-oxo-thieno[3,2-b]pyridine-6-carboxamide;
N-(1-azabicyclo[2,2,2]oct-4-yl)-4,7-dihydro-2,4-dimethyl-7-oxo-thieno[3,2-b]pyridine-6-carboxamide;
N-(1-azabicyclo[2,2,2]oct-4-yl)-4,7-dihydro-3,4-dimethyl-7-oxo-thieno[3,2-b]pyridine-6-carboxamide;
N-(1-azabicyclo[2,2,2]oct-4-yl)-4,7-dihydro-4-ethyl-2-methyl-7-oxo-thieno[3,2-b]pyridine-6-carboxamide;
N-(1-azabicyclo[3,2,2]non-2-yl)-4,7-dihydro-7-oxo-thieno[3,2-b]pyridine-6-carboxamide;
N-(1-azabicyclo[3,2,2]non-2-yl)-4,7-dihydro-4-methyl-7-oxo-thieno[3,2-b]pyridine-6-carboxamide;
N-(1-azabicyclo[3,2,2]non-2-yl)-4,7-dihydro-4-ethyl-7-oxo-thieno[3,2-b]pyridine-6-carboxamide;
N-(1-azabicyclo[3,2,2]non-2-yl)-4,7-dihydro-2,4-dimethyl-7-oxo-thieno[3,2-b]pyridine-6-carboxamide;
N-(1-azabicyclo[3,2,2]non-2-yl)-4,7-dihydro-3,4-dimethyl-7-oxo-thieno[3,2-b]pyridine-6-carboxamide;
N-(1-azabicyclo[3,2,2]non-2-yl)-4,7-dihydro-4-ethyl-2-methyl-7-oxo-thieno[3,2-b]pyridine-6-carboxamide;
N-(1-azabicyclo[3,2,2]non-3-yl)-4,7-dihydro-7-oxo-thieno[3,2-b]pyridine-6-carboxamide;
N-(1-azabicyclo[3,2,2]non-4-yl)-4,7-dihydro-7-oxo-thieno[3,2-b]pyridine-6-carboxamide;
N-(1-azabicyclo[3,2,2]non-5-yl)-4,7-dihydro-7-oxo-thieno[3,2-b]pyridine-6-carboxamide;
N-(1-azabicyclo[3,2,2]non-6-yl)-4,7-dihydro-7-oxo-thieno[3,2-b]pyridine-6-carboxamide; and
N-(1-azabicyclo[3,2,2]non-7-yl)-4,7-dihydro-7-oxo-thieno[3,2-b]pyridine-6-carboxamide.

However, the active ingredients of the therapeutic medicaments of the present invention are not limited to these compounds.

Among them, more preferable compound is R-(−)-N-(1-azabicyclo[2,2,2]oct-3-yl)-4,7-dihydro-7-oxo-thieno[3,2-b]pyridine-6-carboxamide [also referred to as (R)-N-(3-quinuclidinyl)-7-oxo-4,7-dihydrothieno[3,2-b]pyridine-6-carboxamide] or N-oxide thereof. When $R^1$ is hydrogen atom, in the aforementioned formula (I), 4,7-dihydro-7-oxo-thieno [3,2-b]pyridine ring as the heteroaromatic ring may also exist 7-hydroxythieno[3,2-b]pyridine ring as tautomer thereof. Such tautomers also embrace the active ingredients of the therapeutic medicaments of the present invention.

The aforementioned compounds of the active ingredients of the present invention can be prepared according to the methods described in Japanese Patent Unexamined Publication (Kokai) No. Hei 5-310747 (EP560348).

The active ingredients of the therapeutic medicaments of the present invention may be used as pharmaceutically acceptable salts of the aforementioned compounds. Such salts include acid addition salts, quaternary ammonium salts and the like. Such pharmaceutically acceptable acid addition salts include, for example, inorganic acid addition salts such as hydrochloride, hydrobromide, hydroiodide, sulfate, phosphate and the like and organic acid addition salts thereof such as oxalate, maleate, fumarate, lactate, malate, citrate, tartrate, benzoate, methanesulfonate and the like.

The quaternary ammonium salts include, for example, quaternary ammonium salts with lower alkyl halogenides such as methyl iodide such as methyl iodide, methyl bromide, ethyl iodide, ethyl bromide and the like; lower alkyl sulfonate such as methyl methanesulfonate, ethyl methanesulfonate and the like; and lower alkyl arylsulfonates such as methyl p-toluenesulfonate and the like.

The compounds of the formula (I) and pharmaceutically acceptable salts thereof also exist as solvates or hydrates These solvates and hydrates may be used as the active ingredients of the therapeutic medicaments of the present invention.

The aforementioned compounds, pharmaceutically acceptable salts thereof or solvates or hydrates thereof per se can be administered to the patients, and generally it is preferable that the pharmaceutical compositions containing one or not less than two active ingredients are prepared and administered to patients. Such pharmaceutical compositions include pharmaceutical preparations for oral administration such as tablets, capsules, fine granules, powders, pills, troches, sublingual tablets, and liquid preparations and the like and pharmaceutical preparations for parenteral administration such as injections, suppositories, ointments, patches and the like.

Tablets or capsules for oral administration are usually provided in a unit dosage form, and can be prepared by adding conventional pharmaceutical carriers such as binders, fillers, diluents, compressing agents, lubricants, disintegrators, coloring agents, flavoring agents, and moistening agents. The tablets may be coated, for example, by using an enteric coating agent according to the well known methods in the art. For example, fillers such as cellulose, mannitol or lactose; disintegrating agents such as starch, polyvinylpyrrolidone, starch derivatives or sodium starchglycolate; lubricants such as magnesium stearate; and moistening agents such as sodium lauryl sulfate can be used.

Liquid preparations for oral administration can be provided in the form of, for example, aqueous or oily suspensions, solutions, emulsions, syrups and elixirs, as well as dried formulations that is re-dissolvable in water or an appropriate medium before use. Such liquid formulations, conventional additives such as, for example, precipitating preventing agents such as sorbitol, syrup, methyl cellulose, gelatin, hydroxyethylcellulose, carboxymethylcellulose, aluminum stearate gel or hydrogenated edible fat; emulsifiers such as lecithin, sorbitan monooleate or gum arabic; non-aqueous media such as almond oil, refined coconut oil, oily esters (e.g. glycerin esters), propylene glycol or ethyl alcohol (edible oil may be included); preservatives such as methyl ester, ethyl ester or propyl ester of p-hydroxybenzoic acid, or sorbic acid; and, if necessary, conventional flavoring agents or coloring agents.

The pharmaceutical preparations for oral administration can be prepared according to the well known methods in the art such as mixing, filling or compressing. In addition, it is possible to disperse the active ingredient in a preparation containing a large amount of filler by repetitive mixing operation. The pharmaceutical preparations for parenteral administration are generally provided as liquid type unit dosage form preparations containing the compound as the active ingredient and a sterilized medium. The pharmaceutical preparations for parenteral administration can be manufactured by dissolving the compound in the medium, subjecting the solution to filtration for sterilization, filling the resultant solution in suitable vials or ampoules, and then sealing the vials or ampoules. It is possible to freeze the composition, fill it in vials and then removing the moisture in vacuo to improve the stability. Parenteral suspensions can be substantially prepared by the same methods as those applied the parenteral solution and preferably prepared by suspending the active ingredient in a medium, and subjecting the resultant suspension to sterilization by using ethylene oxide or the like. Further, surfactants, moistening agents and the like can also be added so that the uniform dispersion of the active ingredient can be achieved.

Dose of the aforementioned compound as the active ingredient may be decided depending on the purpose of the therapeutic or preventive treatment, sort of the diseases to be treated or prevented, conditions, body weight, age, sex and the like of the patient. In general, about 0.001 to about 10 mg may orally be administered, or about 0.001 to about 10 mg may intravenously be administered to an adult daily. Such doses may be desirably administered once or several times a day as divided portions.

BEST MODE FOR CARRYING OUT THE INVENTION

Figure 1:
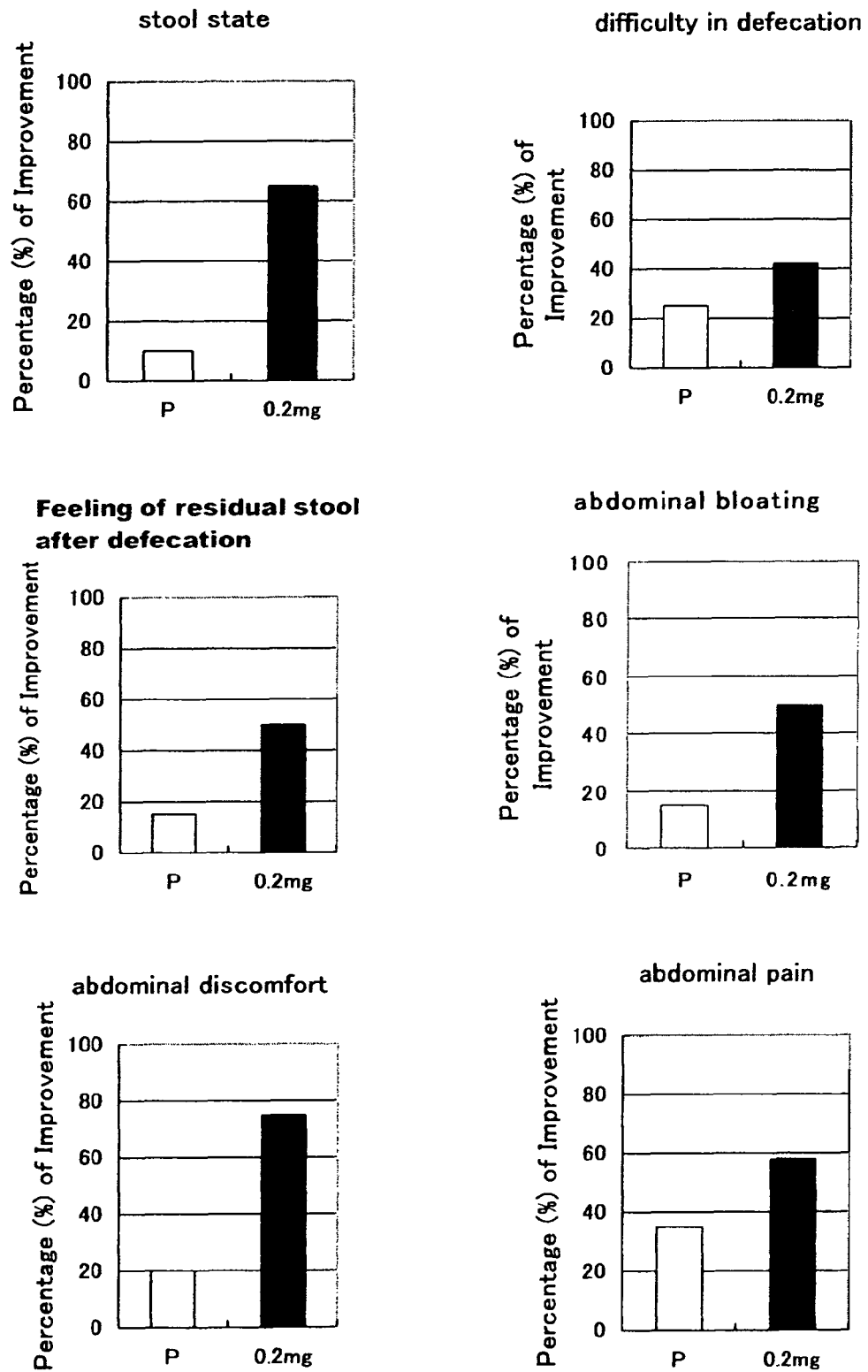
FIG. 1 shows the rate of improvement against each description of stool state, difficulty in defecation, feeling of residual stool after defecation, abdominal bloating, abdominal discomfort and abdominal pain by the administration of placebo and 0.2 mg of the medicament of the present invention. In the Figures, P in the horizontal axis shows the placebo-administration group, and 0.2 mg shows the 0.2 mg administration group of the medicament of the present invention.

The present invention will be explained according to the following examples in more detail. However, the scope of the invention is not limited to these examples. In the following example, (R)-N-(1-azabicyclo[2.2.2]oct-3-yl)-7-hydroxythieno[3,2-b]-pyridine-6-carboxamide (a tautomer of (R)-N-(1-azabicyclo[2.2.2]oct-3-yl)-4,7-dihydro-7-oxo-thieno [3,2-b]pyridine-6-carboxamide) hydrochloride, prepared according to the method described in Example 2 of Japanese Patent Unexamined Publication (Kokai) No. Hei 5-310747 is used as the medicament of the present invention.

EXAMPLE 1

Clinical effects of the medicament of the present invention on patients suffering from constipation predominant IBS were studied (in accordance with Rome II diagnosis criteria).

The test conducted here was a double blind test by two groups. One group was administered with placebo and the other one was administered with 0.2 g (twice a day) of the medicament of the present invention. Administration period consisted of 2-week screening and 4 week treatment. The total impression of the patients upon completion of the treatment was evaluated by 5-scale rating, that is, "highly effective", "moderately effective", "slightly effective", "not effective" and "aggravated". The results are shown in Table 1. In addition, an ameliorating ratio of each symptom, that is, stool state, difficulty in defecation, feeling of residual stool after defecation, abdominal bloating, abdominal discomfort and abdominal pain is shown in FIG. 1

TABLE 1

|  | Highly effective | Moderately effective | Slightly effective | Not effective | Aggravated | Total |
|---|---|---|---|---|---|---|
| Placebo Group | 1 | 2 | 6 | 1 | 0 | 10 |
| 0.2 mg Administration Group | 0 | 5 | 2 | 2 | 0 | 9 |

When the total percentage of the highly effective and moderately effective cases was considered as a ratio of effectiveness, it was 56% in the medicament group, while it was 30% in the placebo group. It has been found from this result that the effectiveness of the former group is about twice as much as that of the placebo group so that it is useful as a remedy for constipation predominant IBS. As is apparent from FIG. 1, the group administered with the medicament of the present invention exhibited an ameliorating ratio exceeding the placebo group in any symptoms typical of constipation predominant IBS. This also suggests that the compound of the present invention is useful as a remedy for constipation type IBS.

The administration results of sennoside, which is a commercially available laxative, to IBS patients are reported in British Journal of Pharmaceutical Practice, 1987 March, pp. 62-64. According to this report, the mean subjective score of sennoside is 2.7. In considering that the score "on the boundary between effective and ineffective (marginal improvement)" is 2 and that of "slightly effective (small improvement)" is 3, that of sennoside exceeds "on the boundary between effective and ineffective (marginal improvement)" but less than "small improvement". It is reported in Clinical Gastroenterology, 2000, VOL. 25, No. 13, p. 1755, that "it is best to avoid the use of stimulant laxatives (sennoside is one of stimulant laxatives) for spastic constipation (constipation predominant IBS) because of their potential to worsen the abdominal pain".

It has been found from the above-described reports that sennoside cannot be expected to have much effect as a remedy for constipation type IBS, or it is not suited for the treatment of constipation predominant IBS. This suggests that laxatives are not always effective for the treatment of constipation type IBS.

INDUSTRIAL APPLICABILITY

The present invention has firstly proved that the medicaments of the present invention have about two fold effective rate than placebo and improved all of the characteristic diseases and symptoms of constipation predominant IBS, and it has made clear that the medicaments of the present invention are useful as the therapeutic medicaments for constipation predominant IBS.

The present application was filed with claiming the conventional priority based on Japanese Patent Application No. 2001-254662.

The invention claimed is:

1. A method of treating constipation predominant IBS comprising administering to a patient in need thereof a therapeutically effective amount of a thieno[3,2-b]pyridinecarboxamide derivative represented by the following formula (I) or a tautomer thereof:

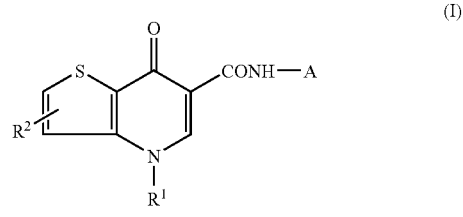

(I)

wherein $R^1$ and $R^2$ each independently represents hydrogen atom or a lower alkyl group and A represents a substituent selected from the group consisting of a 1-azabicyclo[3.2.2] nonyl group, a 1-azabicyclo[2.2.2]octyl group, and N-oxides thereof, or a pharmaceutically acceptable salt thereof.

2. The method according to claim 1 wherein $R^1$ and $R^2$ each independently represents a hydrogen atom or a methyl group.

3. The method according to claim 1, wherein A represents a 1-azabicyclo[2.2.2]oct-3-yl group or an N-oxide thereof.

4. The method according to claim 1, wherein said derivative is any one of N-(1-azabicyclo[2.2.2]oct-3-yl)-4,7-dihydro-7-oxo-thieno[3,2-b]pyridine-6-carboxamide, (R)-N-(1-azabicyclo[2.2.2]oct-3-yl)-4,7-dihydro-7-oxo-thieno[3,2-b]pyridine-6-carboxamide, (S)-N-(1-azabicyclo[2.2.2]oct-3-yl)-4,7-dihydro-7-oxo-thieno[3,2-b]-pyridine-6-carboxamide, or a tautomer thereof.

5. The method according to claim 1, wherein said derivative is in the form of a hydrochloride salt.

6. A method of treating constipation predominant IBS comprising administering to a patient in need thereof a therapeutically effective amount of (R)-N-(1-azabicyclo[2.2.2] oct-3-yl)-4,7-dihydro-7-oxo-thieno[3,2-b]pyridine-6-carboxamide or the tautomer thereof.

7. The method according to claim 2, wherein A represents a 1-azabicyclo[2.2.2]oct-3-yl group or an N-oxide thereof.

8. The method according to claim 2, wherein said derivative is in the form of a hydrochloride salt.

9. The method according to claim 3, wherein said derivative is in the form of a hydrochloride salt.

10. The method according to claim 4, wherein said derivative is in the form of a hydrochloride salt.

11. The method according to claim 6, wherein said derivative is in the form of a hydrochloride salt.

12. The method of claim 1, wherein the derivative of formula (I) is in the form of a pharmaceutically acceptable salt thereof.

13. A method of treating abdominal pain or discomfort associated with constipation predominant IBS, comprising administering to a patient in need thereof a therapeutically effective amount of a thieno[3,2-b]pyridinecarboxamide derivative represented by the following formula (I) or a tautomer thereof:

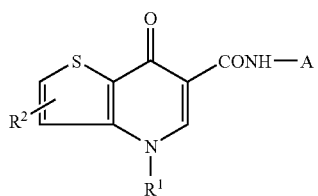

(I)

wherein $R^1$ and $R^2$ each independently represents a hydrogen atom or lower alkyl group and A represents a substituent selected from the group consisting of a 1-azabicyclo[3.2.2]nonyl group, a 1-azabicyclo[2.2.2]octyl group and N-oxides thereof, or a pharmaceutically acceptable salt thereof.

14. The method of claim 13, wherein $R^1$ and $R^2$ each independently represents a hydrogen atom or a methyl group.

15. The method of claim 13, wherein A represents a 1-azabicyclo[2.2.2]oct-3-yl group or an N-oxide thereof.

16. The method of claim 13, wherein said derivative is any one of N-(1-azabicyclo[2.2.2]oct-3-yl)-4,7-dihydro-7-oxo-thieno[3,2-b]pyridine-6-carboxamide, (R)-N-(1-azabicyclo[2.2.2]oct-3-yl)-4,7-dihydro-7-oxo-thieno[3,2-b]pyridine-6-carboxamide, (S)-N-(1-azabicyclo[2.2.2]oct-3-yl)-4,7-dihydro-7-oxo-thieno[3,2-b]pyridine-6-carboxamide, or a tautomer thereof.

17. The method of claim 13, wherein said derivative is in the form of a hydrochloride salt.

18. A method of treating abdominal pain or discomfort associated with constipation predominant IBS, comprising administering to a patient in need thereof a therapeutically effective amount of (R)-N-(1-azabicyclo[2.2.2]oct-3-yl)-4,7-dihydro-7-oxo-thieno[3,2-b]pyridine-6-carboxamide, or the tautomer thereof.

19. The method of claim 18, wherein said derivative is in the form of a hydrochloride salt.

20. The method of claim 13, wherein the administration is oral.

21. The method of claim 13, wherein the derivative of formula (I) is in the form of a pharmaceutically acceptable salt thereof.

* * * * *